United States Patent [19]
Manoharan et al.

[11] Patent Number: 6,043,352
[45] Date of Patent: Mar. 28, 2000

[54] 2'-O-DIMETHYLAMINOETHYLOXYETHYL-MODIFIED OLIGONUCLEOTIDES

[75] Inventors: Muthiah Manoharan, Carlsbad; Phillip Dan Cook, Lake San Marcos, both of Calif.

[73] Assignee: Isis Pharmaceuticals, Inc., Carlsbad, Calif.

[21] Appl. No.: 09/130,566

[22] Filed: Aug. 7, 1998

[51] Int. Cl.$^7$ .................................................. C07H 21/04
[52] U.S. Cl. .............................. 536/24.2; 435/6; 536/24.5
[58] Field of Search ................................ 435/6; 536/26.6, 536/24.2

[56] References Cited

U.S. PATENT DOCUMENTS

| | | | |
|---|---|---|---|
| 3,687,808 | 8/1972 | Merigan et al. | 195/28 N |
| 5,212,295 | 5/1993 | Cook | 536/26.7 |

FOREIGN PATENT DOCUMENTS

WO 89/12060  12/1989  WIPO.

OTHER PUBLICATIONS

Abe, et al., "Conformational Energies and the Random–Coil Dimensions and Dipole Moments of the Polyoxides $CH_3O[(CH_2)_yO]_xCH_3$", *J. Am. Chem. Soc.*, 1976, 98, 6468–6476.

Altmann, et al., "Second Generation of Antisense Oligonucleotides: From Nuclease Resistance to Biological Efficacy in Animals", *Chimia*, 1996, 50, 168–176.

Altmann, et al., "Second–generation antisense oligonucleotides: structure–activity relationships and the design of improved signal–transduction inhibitors", *Biochem. Soc. Trans.*, 1996, 24, 630–637.

Altmann, et al., "Second Generation Antisense Oligonucleotides—Inhibition of PKCα and c–RAF Kinase Expression by Chimeric Oligonucleotides Incorporating 6'–Substituted Carbocyclic Nucleosides and 2'–O–Ethylene Glycol Substituted Ribonucleosides", *Nucleosides & Nucleosides*, 1997, 16, 917–926.

Anderson, et al., Meeting Abstracts, International Hepatitis Meeting, Hawaii, 1997.

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11994–12000.

Beal et al., "Second Structural Motif for Recognition of DNA by Oligonucleotide–Directed Triple–Helix Formation", *Science*, 1991, 251, 1360–1363.

Beaucage, S.L. et al., "Advances in the Synthesis of Oligonucleotides by the Phosphoramidite Approach", *Tetrahedron*, 1992, 48, 2223–2311.

Beese, et al., "Structural basis for the 3'–5' exonuclease activity of *Escherichia coli* DNA polymerase I: a two metal ion mechanism", *EMBO J.*, 1991, 10, 25–33.

Bock, et al., "Selection of single–stranded DNA molecules that bind and inhibit human thrombin", *Nature*, 1992, 355, 564–566.

Brautigam, et al., "Structural Principles for the Inhibition of the 3'–5' Exonuclease Activity of *Escherichia coli* DNA Polymerase I by Phosphorothioates", *J. Mol. Biol.*, 1998, 277, 363–377.

Cohen, J.S. et al., *Oligonucleotides: Antisense Inhibitors of Gene Expression*, 1989, CRC Press, Boca Raton, FL.

Conte, et al., "Conformational properties and thermodynamics of the RNA duplex $r(CGCAAAUUUGCG)_2$: comparison with the DNA analogue $d(CGCAAATTTGCG)_2$", *Nucleic Acids Res.*, 1997, 25, 2627–2634.

Cowsert, L.M., "In vitro and in vivo activity of antisense inhibitors of ras: potential for clinical development", *Anti–cancer drug design*, 1997, 12, 359–371.

Crooke, et al., "Progress in Antisense Therapeutics", *Med. Res. Rev.*, 16, 319–344.

Crooke, S.T. et al., "Pharmacokinetic Properties of Several Novel Oligonucleotide Analogs in mice", *J. Pharmacol. Exp. Therapeutics*, 1996, 277, 923–937.

De Mesmaeker, A. et al., "Antisense Oligonucleotides", *Acc. Chem. Res.*, 1995, 28, 366–374.

Egli, et al., "RNA Hydration: A Detailed Look", *Biochemistry*, 1996, 35, 8489–8494.

Englisch, U. et al., "Chemically Modified Oligonucleotides as Probes and Inhibitors", *Angew. Chem. Int. Ed. Eng.*, 1991, 30, 613–629.

Federoff, et al., "Structure of a DNA: RNA Hybrid Duplex Why Rnase H Does Not Cleave Pure RNA", *J. Mol. Biol.*, 1993, 233, 509–523.

Freier, S.M. et al., "The ups and downs of nucleic acid duplex stability: structure–stability studies on chemically–modified DNA:RNA duplexes", *Nucl. Acids. Res.*, 1997, 25, 4429–4443.

Gonzalez, et al., "Structure and Dynamics of a DNA–RNA Hybrid Duplex with a Chiral Phosphorothioate Moiety: NMR and Molecular Dynamics with Conventional and Time–Averaged Restraints", *Biochemistry*, 1995, 34, 4969–4982.

Griffin, et al., "In Vivo Anticoagulant Properties of a Novel Nucleotide–Based Thrombin Inhibitor and Demonstration of Regional Anticoagulation in Extracorporeal Circuits", *Blood*, 1993, 81, 3271–3276.

Hanecak, et al., "Antisense Oligonucleotide Inhibition of Hepatitis C VirusGene Expression in Transformed Hepatocytes", *J. Virol.*, 1996, 70, 5203–5212.

(List continued on next page.)

*Primary Examiner*—Scott W. Houtteman
*Attorney, Agent, or Firm*—Woodcock Washburn Kurtz Mackiewicz & Norris LLP

[57] ABSTRACT

2'-O-Modified ribosyl nucleosides and modified oligonucleotides containing such nucleotides are disclosed. Oligonucleotides are disclosed that have increased binding affinity as shown by molecular modeling experiments. The 2'-O-modified nucleosides of the invention include ring structures that position the sugar moiety of the nucleosides preferentially in 3' endo geometries.

9 Claims, No Drawings

OTHER PUBLICATIONS

Horton, et al., "The Structure of an RNA/DNA Hybrid: A Substrate of the Ribonuclease Activity of HIV-1 Reverse Transcriptase", *J. Mol. Biol.,* 1996, 264, 521–533.

Kabanov, A. V., "A new class of antivirals: antisense oligonucleotides combined with a hydrophobic substituent effectively inhibit influenza virus reproduction and synthesis of virus–specific proteins in MDCK cells", *FEBS Letts.,* 1990, 259, 327–330.

Kroschwitz, J.I., "Polynucleotides", *Concise Encyclopedia of Polymer Science and Engineering,* 1990, John Wiley & Sons, New York, 858–859.

Lane, et al., "NMR assignments and solution conformation of the DNA–RNA hybrid duplex d(GTGAACTT). r(AAG-UUCAC)", *Eur. J. Biochem.,* 1993, 215, 297–306.

Lesnick, et al., "Relative Thermodynamic Stability of DNA, RNA and DNA: RNA Hybrid Duplexes: Relationship with Base Composition and Structure", *Biochemistry,* 1995, 34, 10807–10815.

Lesnick, E.A. et al., "Oligonucleotides Containing 2'–O–Modified Adenosine" Synthesis and Effects on Stability of DNA–RNA Duplexes , *Biochem.,* 1993, 32, 7832–7838.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.,* 1989, 86, 6553–6556.

Manoharan M. et al., "Cholic Acid–Oligonucliotide Conjugates for Antisense Applications", *Bioorganic Med. Chem. Letts.,* 1994, 4, 1053–1060.

Manoharan, M. et al., "Introduction of Lipophilic Thioether Tether in the Minor Groove of Nucleic Acids for Antisense Applications", *Bioorg. Med. Chem. Letts.,* 1993, 3, 2765–2770.

Manoharan, M. et al., "Lipidic Nucleic Acids", *Tetrahedron Letts.,* 1995, 36, 3651–3654.

Manoharan M. et al., "Oligonucleotide Conjugates: Alteration of the Pharmacokinetic Properties of Antisense Agents", *Nucleosides and Nucleotides,* 1995, 14, 969–973.

Martin, P., "Ein neuer Zugang zu 2'–O–Alkylribonucleosiden und Eigenschaften deren Oligonucleotide", *Helvetica Chemica Acta,* 1995, 78, 486–504.

Miller, P.S. et al., "A New approach to chemotherapy based on molecular biology and nucleic acid chemistry: Matagen (masking tape for gene expression)", *Anti–Cancer Drug Des.,* 1987, 2, 117–128.

Milligan, "Current Concepts in Antisense Drug Design", *J. Med. Chem.,* 1993, 36, 1923–1937.

Mishra, R.K. et al., "Improved leishmanicidal effect of phosphorotioate antisense oligonucleotides by LDL–medicated delivery", *Biochim. et Biophysica,* 1995, 1264, 229–237.

Oberhauser, B. et al., "Effective incorporation of 2'–O–methyl–oligonucleotides into liposomes and enhanced cell association through modification with thiocholesterol", *Nucl. Acids Res.,* 1992, 20, 533–538.

Saison–Behmoaras, T. et al., "Short modified antisense oligonucleotides directed against Ha–ras point mutation induce selective cleavage of the mRNA and inhibit T24 cells proliferation", *EMBO J.,* 1991, 10, 1111–1118.

Sanger, et al., Principles of Nucleic Acid Structure, 1984, Springer–Verlag; New York, NY.

Searle, et al., "On the stability of nucleic acid structures in solution: enthalpy–entropy compensations, internal rotations and reversibility", *Nucleic Acids Res.,* 1993, 21, 2051–2056.

Shea, R.G. et al., "Synthesis, hybridization properties and antiviral activity of lipid–oligodeoxynucletide conjugates", *Nucl. Acids Res.,* 1990, 18, 3777–3783.

Svinarchuk, F.P. et al., "Inhibition of HIV proliferation in MT–4 cells by antisense oligonucleotide conjugated to lipophilic groups", *Biochimie,* 1993, 79, 49–54.

Stein, C.A. et al., "Oligonucleotides as Inhibitors of Gene Expression: A Review", *Cancer Res.,* 1988, 48, 2659–2668.

Uhlmann, E. et al., "Antisense Oligonucleotides: A New Therapeutic Principle", *Chem. Reviews,* 1990, 90, 544–584.

Wagner, et al., "Antisense Gene Inhibition by Oligonucleotides Containing C–5 Propyne Pyrimidines", *Science,* 1993, 260, 1510–1513.

Wolfe, et al., "The Gauche Effect. Some Stereochemical Consequences of Adjacent Electron Pairs and Polar Bonds", *Acc. Chem. Res.,* 1972, 5, 102–111.

Young, et al., "Triple helix formation inhibits transcription elongation in vitro", *Proc. Natl. Acad. Sci.,*1991, 88, 10023–10026.

2'-O-DIMETHYLAMINOETHYLOXYETHYL-MODIFIED OLIGONUCLEOTIDES

FIELD OF THE INVENTION

The present invention relates to nucleosides, oligonucleotides incorporating such nucleosides, and methods of using such oligonucleosides. The oligonucleotides of the invention are useful in therapeutic and for investigative purposes. More specifically, the present invention is directed to the use of oligonucleotides having 2'-O-modifications that will increase affinity and nuclease resistance.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. Recently, however, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents with great promise, and are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells (see, e.g., Wagner et al., Science (1993) 260: 1510–1513; Milligan et al., *J. Med. Chem.*, (1993) 36:1923–37; Uhlmann et al., *Chem. Reviews*, (1990) 90:543–584; Stein et al., *Cancer Res.*, (1988) 48:2659–2668).

The events that provide the disruption of the nucleic acid function by antisense oligonucleotides (Cohen in *Oligonucleotides: Antisense Inhibitors of Gene Expression*, (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides: Miller, P. S. and Ts'O, P.O.P. (1987) *Anti-Cancer Drug Design*, 2:117–128, and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Oligonucleotides may also bind to duplex nucleic acids to form triplex complexes in a sequence specific manner via Hoogsteen base pairing (Beal et al., *Science*, (1991) 251:1360–1363; Young et al., *Proc. Natl. Acad. Sci.* (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity).

Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as "aptamers" and they typically bind to and interfere with the function of protein targets (Griffin, et al., *Blood*, (1993), 81:3271–3276; Bock, et al., *Nature*, (1992) 355: 564–566).

Oligonucleotides and their analogs have been developed and used for diagnostic purposes, therapeutic applications and as research reagents. For use as therapeutics, oligonucleotides preferably are transported across cell membranes or be taken up by cells, and appropriately hybridize to target DNA or RNA. These functions are believed to depend on the initial stability of the oligonucleotides toward nuclease degradation. A deficiency of unmodified oligonucleotides which affects their hybridization potential with target DNA or RNA for therapeutic purposes is their degradation by a variety of ubiquitous intracellular and extracellular nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and resist nuclease degradation. Modifications have been made, for example, to the phosphate backbone to increase the resistance to nucleases. These modifications include use of linkages such as methyl phosphonates, phosphorothioates and phosphoro-dithioates, and the use of modified sugar moieties such as 2'-O-alkyl ribose. Other oligonucleotide modifications include those made to modulate uptake and cellular distribution. A number of modifications that dramatically alter the nature of the internucleotide linkage have also been reported in the literature. These include non-phosphorus linkages, peptide nucleic acids (PNA's) and 2'–5' linkages. Another modification to oligonucleotides, usually for diagnostic and research applications, is labeling with non-isotopic labels, e.g., fluorescein, biotin, digoxigenin, alkaline phosphatase, or other reporter molecules.

Over the last ten years, a variety of synthetic modifications have been proposed to increase nuclease resistance, or to enhance the affinity of the antisense strand for its target mRNA (Crooke et al., *Med. Res. Rev.*, 1996, 16, 319–344; De Mesmaeker et al., *Acc. Chem. Res.*, 1995, 28, 366–374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased ybrid stability.

RNA exists in what has been termed "A Form" geometry while DNA exists in "B Form" geometry. In general, NA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2'-methoxyethoxy (MOE, 2'-OCH$_2$CH$_2$OCH$_3$) side chain (Baker et al., *J. Biol. Chem.*, 1997, 272, 11944–12000; Freier et al., *Nucleic Acids Res.*, 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429–4443). 2'-O-Methoxyethyl-substituted also have been shown to be antisense inhibitors of gene expression with promising features for in vivo use (Martin, P., *Helv. Chim. Acta*, 1995, 78, 486–504; Altmann et al., *Chimia*, 1996, 50, 168–176; Altmann et al., *Biochem. Soc. Trans.*, 1996, 24, 630–637; and Altmann et al., *Nucleosides Nucleotides*, 1997, 16, 917–926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

Although the known modifications to oligonucleotides, including the use of the 2'-O-methoxyethyl modification, have contributed to the development of oligonucleotides for various uses, there still exists a need in the art for further modifications to oligonucleotides having enhanced hybrid binding affinity and/or increased nuclease resistance.

SUMMARY OF THE INVENTION

The present invention provides nucleotides and oligonucleotides which bear 2'-O-[2-(2-N,N-dimethylaminoethyl)oxyethyl]-5-methyl (2'-O-DMAEOE) substituents. Preferred oligonucleotides of the invention are those that include at least one nucleotide of the formula:

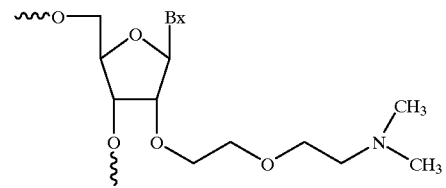

wherein Bx is a heterocyclic base. In certain embodiments of the invention, the heterocyclic base is a purine or a pyrimidine, preferably adenine, cytosine, 5-methylcytosine, thymine, uracil, guanine or 2-aminoadenine. The oligonucleotides preferably comprise from about 5 to about 50 nucleosides, more preferably from about 8 to about 30 nucleosides, even more preferably from about 15 to about 25 nucleosides.

The present invention also provides compounds having the formula:

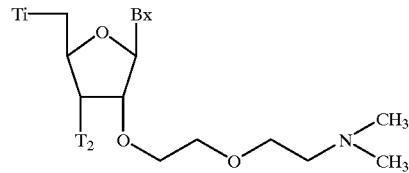

wherein Bx is a heterocyclic base; and T$_1$ and T$_2$, independently, are OH, a protected hydroxyl, an activated phosphate group, an activated phosphite group, a reactive group for forming an internucleotide linkage, a nucleotide, a nucleoside, or an oligonucleotide. The heterocyclic base can be a purine or a pyrimidine, such as adenine, cytosine, 5-methylcytosine, thymine, uracil, guanine or 2-aminoadenine.

DETAILED DESCRIPTION OF THE INVENTION

The present invention is directed to novel 2'-O-modified nucleotides and to oligonucleotides incorporating these novel nucleotides. These modifications have certain desirable properties that contribute toward increases in binding affinity and/or nuclease resistance.

There are a number of items to consider when designing oligonucleotides having enhanced binding affinities. One effective approach to constructing oligonucleotides with very high RNA binding affinity relates to the combination of two or more different types of modifications, each of which contributes favorably to various factors that might be important for binding affinity.

Freier and Altmann, *Nucleic Acids Research*, (1997) 25:4429–4443, recently published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and $T_m$. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Numerous backbone modifications were also investigated including backbones bearing phosphorus, backbones that did not bear a phosphorus atom, and backbones that were neutral.

Four general approaches potentially may be used to improve hybridization of oligonucleotides to RNA targets. These include: preorganization of the sugars and phosphates of the oligodeoxynucleotide strand into conformations favorable for hybrid formation, improving stacking of nucleobases by the addition of polarizable groups to the heterocycle bases of the nucleotides of the oligonucleotide, increasing the number of H-bonds available for A-U pairing, and neutralization of backbone charge to facilitate removing undesirable repulsive interactions. This invention principally employs the first of these, preorganization of the sugars and phosphates of the oligodeoxynucleotide strand into conformations favorable for hybrid formation, and can be used in combination with the other three approaches.

Sugars in DNA:RNA hybrid duplexes frequently adopt a C3' endo conformation. Thus, modifications that shift the conformational equilibrium of the sugar moieties in the single strand toward this conformation should preorganize the antisense strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This pucker conformation further assisted in increasing the Tm of the oligonucleotide with its target.

There is a clear correlation between substituent size at the 2'-position and duplex stability. Incorporation of alkyl substituents at the 2'-position typically leads to a significant decrease in binding affinity. Thus, small alkoxy groups generally are very favorable while larger alkoxy groups at the 2'-position generally are unfavorable. However, if the 2'-substituent contained an ethylene glycol motif, then a strong improvement in binding affinity to the target RNA is observed.

The high binding affinity resulting from 2'-substitution has been partially attributed to the 2'-substitution causing a C3' endo sugar pucker which in turn may give the oligomer a favorable A-form like geometry. This is a reasonable hypothesis since substitution at the 2' position by a variety of electronegative groups (such as fluoro and O-alkyl chains) has been demonstrated to cause C3' endo sugar puckering (De Mesmaeker et al., *Acc. Chem. Res.*, 1995, 28, 366–374; Lesnik et al., *Biochemistry*, 1993, 32, 7832–7838).

In addition, for 2'-substituents containing an ethylene glycol motif, a gauche interaction between the oxygen atoms around the O-C-C-O torsion of the side chain may have a stabilizing effect on the duplex (Freier et al.,*Nucleic Acids Research*, (1997) 25:4429–4442). Such gauche interactions have been observed experimentally for a number of years (Wolfe et al., *Acc. Chem. Res.*, 1972, 5, 102; Abe et al., *J. Am. Chem. Soc.*, 1976, 98, 468). This gauche effect may result in a configuration of the side chain that is favorable for duplex formation. The exact nature of this stabilizing configuration has not yet been explained. While we do not want to be bound by theory, it may be that holding the O-C-C-O torsion in a single gauche configuration, rather than a more random distribution seen in an alkyl side chain, provides an entropic advantage for duplex formation.

The 2'-O-[2-(2-N,N-dimethylaminoethyl)oxyethyll-5-methyl (2'-O-DMAEOE)side chain of the present invention additionally has the —$CH_2CH_2$—$N(CH_2)$ $(CH_2)$, which has a tertiary amine that can become protonated. The pKa of the 2'-O-[2-(2-N,N-dimethylaminoethyl)oxyethyl]-5-methyl side chain of the present invention is 9.0 to 10.0 (aliphatic saturated 3° amine). This tertiary (3°) amine is expected to be protonated at physiological pH (7.0), and in endosomes and lysosomes (pH 5.0). The resulting positive charge should improve the biostability of the drug by either inhibiting the nuclease from binding to the oligonucleotide or displacing the metal ions needed for the nucleases to carry on their function (Beese et al., *EMBO J.*, 1991, 10, 25–33; and Brautigam et al., *J. Mol. Bio.*, 1998, 277, 363–377).

The nucleosides and oligonucleotides can include modified sugars and modified bases. (See, e.g., U.S. Pat. No. 3,687,808 and PCT application PCT/US89/02323) Such oligonucleotides are best described as being structurally distinguishable from, yet functionally interchangeable with, naturally occurring or synthetic wild type oligonucleotides. Representative modified sugars include carbocyclic or acyclic sugars, sugars having substituent groups at their 2' position, sugars having substituent groups at their 3' position, and sugars having substituents in place of one or more hydrogen atoms of the sugar. Representative heterocyclic base moieties amenable to the present invention include guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613. All such oligonucleotides are comprehended by this invention so long as they function effectively to mimic the structure of a desired RNA or DNA strand.

Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocyclic ring" denotes an alkyl ring system having one or more heteroatoms (i.e., non-carbon atoms). Preferred heterocyclic rings include, for example but not limited to imidazole, pyrrole, 1,3-dioxane, pyrazole, indole, 1H-indazole, α-carboiine, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups As used herein, the term "heterocyclic ring" also denotes a ring system having one or more double bonds, and one or more heteroatoms. Preferred heterocyclic rings include, for example but not limited to the pyrrolidino ring.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

The oligonucleotides of the present invention can be used in diagnostics, therapeutics and as research reagents. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes RNA-DNA transcription or RNA-protein translation as a fundamental part of its hereditary, metabolic or cellular control is susceptible to therapeutic and/or prophylactic treatment in accordance with this invention. Seemingly diverse organisms such as bacteria, yeast, protozoa, algae, all plants and all higher animal forms including warm-blooded animals, ca be treated. Further each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

Oligonucleotides according to the invention can be assembled in solution or through solid-phase reactions, for example, on a suitable DNA synthesizer utilizing nucleosides, phosphoramidites and derivatized controlled pore glass (CPG) according to the invention and/or standard nucleotide precursors. In addition to nucleosides that include a novel modification of the inventions other nucleoside within an oligonucleotide may be further modified with other modifications at the 2' position. Precursor nucleoside and nucleotide precursors used to form such additional modification may carry substituents either at the 2' or 3' positions. Such precursors may be synthesized according to the present invention by reacting appropriately protected nucleosides bearing at least one free 2' or 3' hydroxyl group with an appropriate alkylating agent such as, but not limited to, alkoxyalkyl halides, alkoxylalkylsulfonates, hydroxyalkyl halides, hydroxyalkyl sulfonates, aminoalkyl halides, aminoalkyl sulfonates, phthalimidoalkyl halides, phthalimidoalkyl sulfonates, alkylaminoalkyl halides, alkylaminoalkyl sulfonates, dialkylaminoalkyl halides, dialkylaminoalkylsulfonates, dialkylaminooxyalkyl halides, dialkylaminooxyalkyl sulfonates and suitably protected versions of the same. Preferred halides used for alkylating reactions include chloride, bromide, fluoride and iodide. Preferred sulfonate leaving groups used for alkylating reactions include, but are not limited to, benzenesulfonate, methylsulfonate, tosylate, p-bromobenzenesulfonate, triflate, trifluoroethylsulfonate, and (2,4-dinitroanilino)-benzenesulfonate.

Suitably protected nucleosides can be assembled into oligonucleotides according to known techniques. See, for example, Beaucage et al., *Tetrahedron*, 1992, 48, 2223.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, *Nucl. Acids Research*, 1997, 25, 4429–443).

The relative binding ability of the oligonucleotides of the present invention was determined using protocols as described in the literature (Freier and Altmann, *Nucl. Acids Research*, 1997, 25, 4429–443). Typically absorbance versus temperature curves were determined using samples containing 4 uM oligonucleotide in 100 mM Na+, 10 mM phosphate, 0.1 mM EDTA, and 4 uM complementary, length matched RNA.

The in vivo stability of oligonucleotides is an important factor to consider in the development of oligonucleotide therapeutics. Resistance of oligonucleotides to degradation by nucleases, phosphodiesterases and other enzymes is therefore determined. Typical in vivo assessment of stability of the oligonucleotides of the present invention is performed by administering a single dose of 5 mg/kg of oligonucleotide in phosphate buffered saline to BALB/c mice. Blood collected at specific time intervals post-administration is analyzed by HPLC or capillary gel electrophoresis (CGE) to determine the amount of oligonucleotide remaining intact in circulation and the nature the of the degradation products.

Heterocyclic bases amenable to the present invention include both naturally and non-naturally occurring nucleobases and heterocycles. A representative list includes adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further heterocyclic bases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

2'-O-[2(2-N,N-dimethylaminoethoxy)ethyl]-5-methyl uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. Hydrogen gas evolved as the solid dissolved $O^{2-}$, 2'-anhydro-5-methyluridine (1.2 g, 5 mmol), and sodium bicarbonate (2.5 mg) were added and the bomb was sealed, placed in an oil bath and heated to 155° C. for 26 hours. The bomb was cooled to room temperature and opened. The crude solution was concentrated and the residue partitioned between water (200 mL) and hexanes (200 mL). The excess phenol was extracted into the hexane layer. The aqueous layer was extracted with ethyl acetate (3×200 mL) and the combined organic layers were washed once with water, dried over anhydrous sodium sulfate and concentrated. The residue was columned on silica gel using methanol/methylene chloride 1:20 (which has 2% triethylamine) as the eluent. As the column fractions were concentrated a colorless solid formed which was collected to give 490 mg of the title compound as a white solid. Rf=0.56 in $CH_2$—$CH_{12}$:$CH_3$—OH (10:1); MS/ES calculated 374; observed 374.5.

EXAMPLE 2

5'-O-dimethoxytrityl-2'-O-[2(2-N,N-dimethylaminoethoxy)ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) were added and stirred for 1 hour. The reaction mixture was poured into water (200 mL) and extracted with $CH_2Cl_2$; (2×200 mL). The combined $CH_2Cl_2$ layers were washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gave 0.72 g (82%) of the title compound.

EXAMPLE 3

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidate Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture was stirred overnight and the solvent evaporated. The resulting residue was purified by silica gel flash column chromatography with ethyl acetate as the eluent to give 1.98 g (83% yield) of the title compound.

EXAMPLE 4

5'-O-Dimethoxytrityl-2'-O-[2(2-N,N-dimethylaminoethoxy)ethyl)]-5-methyl-uridine-3'-O-succinate 5'-O-Dimethoxytrityl-2'-O-[2(2-N,N-dimethylaminoethoxy)ethyl)]-5-methyluridine (270 mg, 0.41 mmol) was heated with 68 mg of succinic anhydride (0.6 mmol), 4-N,N-dimethylamino pyridine (24 mg) and $Et_3N$ (56 μL) in dichloroethane (1 mL) at 50° C. for 10 minutes in a Pyrex tube in a heating block. After cooling, the reaction mixture was diluted with methylene chloride (20 mL) and washed with a 10% aqueous solution of citric acid (3×20 mL) followed by water. The resulting solution was dried over anhydrous $Na_2SO_4$ to give 217 mg (58% yield) of the title compound.

TLC indicated ($CH_2Cl_2$/MeOH, 10:1) a polar product at the origin, as expected.

EXAMPLE 5

5'-O-Dimethoxytrityl-2'-O-[2(2-N,N-dimethylaminoethoxy)ethyl)]-5-methyl-uridine-3'-O-succinyl controlled pore glass (CPG)

5'-O-Dimethoxytrityl-2'-O-[2(2-N,N-dimethylaminoethoxy)ethyl)]-5-methyl-uridine-3'-O-succinate (116 mg, 0.15 mmol, 2 eq.) was dried under high vacuum overnight. To this dried material was added CPG (650 mg, 1 eq.), anhydrous DMF (2 mL), N-methylmorpholine (33 μL, 4 eq.) and 2-1H-benzotriazole-1-yl (TBTU, 48 mg, 2 eq.). 1,1,3,3-tetramethyluroniumtetrafluoroborate was added to the reaction mixture with shaking for 12 hours. The CPG was then filtered and washed with DMF, $CH_2Cl_2$, $CH_3CN$ and $Et_2O$. Finally, it was dried and capped with acetic anhydride/$Et_3N$. The loading of the CPG was determined via the dimethoxytrityl assay method to be 53 μmoles/g.

EXAMPLE 6

2-[2-(dimethylamino)ethylmercapto]ethanol 2-(Dimethylamino)ethanethiol hydrochloride (Aldrich) is treated with NaOH (0.2N) in ethanol (95%). To this slurry, 2-bromoethanol (1.2 eq.) is added and the mixture is refluxed for 2 hours. The reaction mixture is cooled, filtered and concentrated. The resultant residue is purified by silica gel flash column chromatography to give the title compound.

EXAMPLE 7

2'-O-[2-[2-((dimethylamino)ethyl)mercapto]ethyl)-5-methyl uridine

2-[2-((dimethylamino)ethyl)mercapto] ethanol (50 mmol) is slowly added to a solution of borane in tetrahydrofuran (1 M, 10 mL, 10 mmol) with stirring in a 100 mL bomb. Hydrogen gas is evolved as the solid dissolves. $O^2$, 2'-anhydro-5-methyluridine (1.2 g, 5 mmol), and sodium bicarbonate (2.5 mg) are added and the bomb is sealed, then placed in an oil bath and heated to 155° C. for 26 hours. The bomb is cooled to room temperature and opened. The crude solution is concentrated and the residue partitioned between water (200 mL) and hexanes (200 mL). The excess phenol is extracted into hexanes. The aqueous layer is extracted with ethyl acetate (3×200 mL) and the combined organic layer is washed once with water and dried over anhydrous sodium sulfate and concentrated. The resultant residue is purified by silica gel flash column chromatography using methanol/-methylene chloride having 2% triethylamine to give the title compound.

EXAMPLE 8

5'-O-Dimethoxytrityl-2'-O-2-[2-((dimethylamino)ethyl)mercapto)ethyl)]5-methyl uridine To 2'-O-2-[2-((dimethylamino)ethyl)mercapto]ethyl)]5-methyl uridine (1.3 mmol) in anhydrous pyridine (8 mL), triethylamine (0.36 mL) and DMT-Cl (0.87 g, 2 eq.) are added and stirred for 1 hour. The reaction mixture is poured into water (200 mL) and extracted with $CHMCl$, (2×200 mL). The combined $CH_2Cl_2$ layers are washed with saturated $NaHCO_3$ solution, saturated NaCl solution, dried over anhydrous sodium sulfate and concentrated. The resultant residue is purified by silica gel flash column chromatography using methanol/methylene chloride having 1% triethylamine to give the title compound.

EXAMPLE 9

5'-O-Dimethoxytrityl-2'-O-2-[2-((dimethylamino)ethyl)mercapto]ethyl)]5-methyl uridine-3'-O-(cyanoethyl-N,N-diisopropyl) phosphoramidate 5'-O-Dimethoxytrityl-2'-O-2-[2-((dimethylamino)ethyl)mercapto]ethyl)]5-methyluridine (3 mmol) is dissolved in $CH_2Cl_2$ (20 mL) and to this solution, under argon, diisopropylaminotetrazolide (0.6 g) and 2-cyanoethoxy-N,N-diisopropyl phosphoramidite (1.1 mL, 2 eq.) are added. The reaction is stirred overnight and the solvent is evaporated. The resultant residue is purified by silica gel flash column chromatography using ethyl acetate to give the title phosphoramidite.

EXAMPLE 10

5'-O-Dimethoxytrityl-2'-O-2-[2-((dimethylamino)ethyl)mercapto]ethyl)]5-methyl-uridine-3'-O-succinate 5'-O-Dimethoxytrityl-2'-O-2-[2-((dimethylamino)ethyl)mercapto]ethyl)]5-methyluridine (0.41 mmol) is heated with succinic anhydride (68 mg, 0.6 mmol), 4-N,N-dimethylamino pyridine (24 mg) and $Et_N$ (56 μL) in dichloroethane (1 mL) at 50° C. for 10 minutes in a Pyrex tube in a heating block. After cooling the reaction mixture is diluted with methylene chloride (20 mL) and washed with 10% citric acid aqueous solution (3×20 mL) followed by water and dried over anhydrous $Na_2SO_4$ to give the title succinate.

EXAMPLE 11

5'-O-Dimethoxytrityl-2'-O-2-[2-((dimethylamino) ethyl)mercapto]ethyl)]5-methyl-uridine-3'-O-succinyl controlled pore glass (CPG)

The succinate from Example 10 above (0.15 mmol, 2 eq.) is dried under vacuum overnight. CPG (650 mg, 1 eq.), anhydrous DMF (2 mL), 33 μL of N-methylmorpholine (4 eq.) and 48 mg (2 eq.) of TBTU (2-1H-benzotriazole-1-yl) are added to the dried succinate. 1,1,3,3-tetramethyluronium-tetrafluoroborate is added and the mixture is shaken for 12 hours. The CPG is then filtered and washed with DMF, $CH_2Cl_2$, $CH_3CN$ and $Et_2O$. The CPG is dried and capped with acetic anhydride/$Et_3N$. The loading is determined using the standard dimethoxytrityl assay.

EXAMPLE 12

General Procedures for Oligonucleotide Synthesis

Oligonucleotides are synthesized on a PerSeptive Biosystems Expedite 8901 Nucleic Acid Synthesis System. Multiple 1-mmol syntheses are performed for each oligonucleotide. The 3'-end nucleoside containing solid support is loaded into the column. Trityl groups are removed with trichloroacetic acid (975 mL over one minute) followed by an acetonitrile wash. The oligonucleotide is built using a modified diester or thioate protocol.

Phosphodiester Protocol

All standard amidites (0.1 M) are coupled over a 1.5 minute time frame, delivering 105 μL material. All novel amidites are dissolved in dry acetonitrile (100 mg of amidite/1 mL acetonitrile) to give approximately 0.08–0.1 M solutions. The 2'-modified amidite is double coupled using 210 μL over a total of 5 minutes. Total coupling time is approximately 5 minutes (210 mL of amidite delivered). 1-H-tetrazole in acetonitrile is used as the activating agent. Excess amidite is washed away with acetonitrile. (1S)-(+)-(10-camphorsulfonyl) oxaziridine (CSO, 1.0 g CSO/8.72 mL dry acetonitrile) is used to oxidize (3 minute wait step) delivering approximately 375 μL of oxidizer. Standard amidites are delivered (210 μL) over a 3-minute period.

Phosphorothioate Protocol

The 2'-modified amidite is double coupled using 210 μL over a total of 5 minutes. The amount of oxidizer, 3H-1,2-benzodithiole-3-one-1,1-dioxide (Beaucage reagent, 3.4 g Beaucage reagent/200 mL acetonitrile), is 225 μL (one minute wait step). The unreacted nucleoside is capped with a 50:50 mixture of tetrahydrofuran/acetic anhydride and tetrahydrofuran/pyridine/1-methyl imidazole. Trityl yields are followed by the trityl monitor during the duration of the synthesis. The final DMT group is left intact. After the synthesis, the contents of the synthesis cartridge (1 mmole) is transferred to a Pyrex vial and the oligonucleotide is cleaved from the controlled pore glass (CPG) using 30% ammonium hydroxide ($NH_4OH$, 5 mL) for approximately 16 hours at 55° C.

Oligonucleotide Purification

After the deprotection step, the samples are filtered from CPG using Gelman 0.45 μm nylon acrodisc syringe filters. Excess $NH_4OH$ is evaporated away in a Savant AS160 automatic speed vac. The crude yield is measured on a Hewlett Packard 8452A Diode Array Spectrophotometer at 260 nm. Crude samples are then analyzed by mass spectrometry (MS) on a Hewlett Packard electrospray mass spectrometer. Trityl-on oligonucleotides are purified by reverse phase preparative high performance liquid chromatography (HPLC). HPLC conditions are as follows: Waters 600E with 991 detector; Waters Delta Pak C4 column (7.8×300mm); Solvent A: 50 mM triethylammonium acetate (TEA-Ac), pH 7.0; Solvent B: 100% acetonitrile; 2.5 mL/min flow rate; Gradient: 5% B for first five minutes with linear increase in B to 60% during the next 55 minutes. Fractions containing the desired product/s (retention time= 41 minutes for DMT-ON-16314; retention time=42.5 minutes for DMT-ON-16315) are collected and the solvent is dried off in the speed vac. Oligonucleotides are detritylated in 80% acetic acid for approximately 60 minutes and lyophilized again. Free trityl and excess salt are removed by passing detritylated oligonucleotides through Sephadex G-25 (size exclusion chromatography) and collecting appropriate samples through a Pharmacia fraction collector. The solvent is again evaporated away in a speed vac. Purified oligonucleotides are then analyzed for purity by CGE, HPLC (flow rate: 1.5 mL/min; Waters Delta Pak C4 column, 3.9×300mm), and MS. The final yield is determined by spectrophotometer at 260 nm.+

PROCEDURES

Procedure 1

ICAM-1 Expression

Oligonucleotide Treatment of HUVECs: Cells were washed three times with Opti-MEM (Life Technologies, Inc.) prewarmed to 37° C. Oligonucleotides were premixed with 10 μg/mL Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/mL TNF-α® & D Systems). Incubation at 37° C. was continued until the indicated times.

Quantitation of ICAM-1 Protein Expression by Fluorescence-activated Cell Sorter: Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 μl/$10^5$ cells of the ICAM-1 specific antibody, CD54-PE (Pharmingin). Antibodies were incubated with the cells for 30 min at 4° C. in the dark, under gently agitation. Cells were washed by centrifugation procedures and then resuspended in 0.3 mL of FacsFlow buffer (Becton Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)–(basal ICAM-1 value)/(non-treated ICAM-1 value)–(basal ICAM-1 value)]. (Baker, Brenda, et. al. 2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells, *The Journal of Biological Chemistry*, 272, 11994–12000, 1997.)

ICAM-1 expression of 2'-O-[2-(2-N,N-dimethylaminoethyl)oxyethyl]-5-methyl modified oligonucleotides of the invention is measured by the reduction of ICAM-1 levels in treated HUVEC cells. The oligonucleotides are believed to work by a direct binding RNase H independent mechanism. Appropriate scrambled control oligonucleotides are used as controls. They have the same base composition as the test sequence.

Sequences that contain the 2'-O-[2-(2-N,N-dimethylaminoethyl)oxyethyl]-5-methyl modification as listed in Table 1 below are prepared and tested in the above assay. SEQ ID NO: 3, a C-raf targeted oligonucleotide, is used as a control.

TABLE 1

Oligonucleotides Containing 2'-O-[2-(2-N,N-dimethyl aminoethyl)oxyethyl]-5-methyl modification

| SEQ ID NO: | Sequence (5'-3') | Target |
|---|---|---|
| 1 | 5'-$T_sC^m_sT_sG_sA_sG_sT_sA_sG_sC^m_s$ $A_sG_sA_sG_sG_sA_sG_sC^m_sT_sC$-3' | Human ICAM-1 |
| 2 | 5'-$T_oC^m_oT_oG_oA_oT_oA_oG_oC^m_o$ $A_oG_oA_oG_oG_oA_oG_oC^m_oT_oC$-3' | Human ICAM-1 |
| 3 | 5'-$A_sT_sG_sC^m_sA_sT_sT_sC_s^mT_sG_sC_s^mC_s^mC_s^mC^m_s$ $C^m_sA_sA_sG_sG_sA$-3' | mouse C-raf |
| 4 | 5'-$G_sC^m_sC^m_sC^m_sA_sA_sG_sC^m_sT_sG_sG_sC^m_s$ $A_sT_sC^m_sC^m_sG_sT_sC^m_sA$-3' | Human ICAM-1 |

All nucleosides in bold are 2'-O-[2-(2-N,N-dimethylaminoethyl)oxyethyl]-5-methyl; subscript S indicates a phosphorothioate linkage; subscript O indicates a phosphodiester linkage; and a superscript m on a C ($C^m$) indicates a 5-methyl-C.

Procedure 2

Enzymatic Degradation of 2'-O-modified Oligonucleotides

Three oligonucleotides are synthesized incorporating the modifications to the 3' nucleoside at the 2'-O- position (Table 2). These modified oligonucleotides are subjected to snake venom phosphodiesterase to determine their nuclease resistance. Oligonucleotides (30 nanomoles) are dissolved in 20 mL of buffer containing 50 mM Tris-HCl pH 8.5, 14 mM $MgCl_2$ and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) are added and the reaction mixture is incubated at 37° C. for 100 hours. HPLC analysis is carried out using a Waters model 715 automatic injector, model 600E pump, model 991 detector, and an Alltech (Alltech Associates, Inc., Deerfield, Ill.) nucleoside/nucleotide column (4.6×250 mm). All analyses are performed at room temperature. The solvents used are A: water and B: acetonitrile. Analysis of the nucleoside composition is accomplished with the following gradient: 0–5 min., 2% B (isocratic); 5–20 min., 2% B to 10% B (linear); 20–40 min., 10% B to 50% B. The integrated area per nanomole is determined using nucleoside standards. Relative nucleoside ratios are calculated by converting integrated areas to molar values and comparing all values to thymidine, which is set at its expected value for each oligomer.

TABLE 2

Relative Nuclease Resistance of 2'-Modified Chimeric Oligonucleotides

SEQ ID NO 5; 5'-TTT TTT TTT TTT TTT T*T*T*T*-3' (Uniform phosphodiester)

| T* = 2'-modified T | 2'-O- Modification |
|---|---|
| —O—$CH_2$—$CH_2$—$CH_3$ | Pr |
| —O—$CH_2$—$CH_2$—O—$CH_3$ | MOE |
| —O—(DMAEOE) | DMAEOE |

Procedure 3

General Procedure for the Evaluation of Gapped 2'-O-DMAEOE Modified Oligonucleotides Targeted to Ha-ras Different types of human tumors, including sarcomas, neuroblastomas, leukemias and lymphomas, contain active oncogenes of the ras gene family. Ha-ras is a family of small molecular weight GTPases whose function is to regulate cellular proliferation and differentiation by transmitting signals resulting in constitutive activation of ras are associated with a high percentage of diverse human cancers. Thus, ras represents an attractive target for anticancer therapeutic strategies.

SEQ ID NO: 6 is a 20-base phosphorothioate oligodeoxynucleotide targeting the initiation of translation region of human Ha-ras and it is a potent isotype-specific inhibitor of Ha-ras in cell culture based on screening assays ($IC_{50}$=45 nm). Treatment of cells in vitro with SEQ ID NO: 6 results in a rapid reduction of Ha-ras mRNA and protein synthesis and inhibition of proliferation of cells containing an activating Ha-ras mutation. When administered at doses of 25 mg/kg or lower by daily intraperitoneal injection (IP), SEQ ID NO: 6 exhibits potent antitumor activity in a variety of tumor xenograft models, whereas mismatch controls do not display antitumor activity. SEQ ID NO: 6 has been shown to be active against a variety of tumor types, including lung, breast, bladder, and pancreas in mouse xenograft studies (Cowsert, L. M. *Anti-cancer drug design*, 1997, 12, 359–371). A second-generation analog of SEQ ID NO: 6, where the 5' and 3' termini ("wings") of the sequence are modified with 2'-methoxyethyl (MOE) modification and the backbone is kept as phosphorothioate (Table 2, SEQ ID NO: 12), exhibits $IC_{50}$ of 15 nm in cell culture assays. thus, a 3-fold improvement in efficacy is observed from this chimeric analog. Because of the improved nuclease resistance of the 2'-MOE phosphorothioate, SEQ ID NO: 12 increases the duration of antisense effect in vitro. This will relate to frequency of administration of this drug to cancer patients. SEQ ID NO: 12 is currently under evaluation in ras dependent tumor models (Cowsert, L. M. *Anti-cancer drug design*, 1997, 12, 359–371). The parent compound, SEQ ID NO: 6, is in Phase I clinical trials against solid tumors by systemic infusion. Antisense oligonucleotides having the 2'-O-DMAEOE modification are prepared and tested in the aforementioned assays in the manner described to determine activity. Oligonucleotides that are initially prepared are listed in Table 3 below.

TABLE 3

Ha-ras Antisense Oligonucleotides With 2'-O-DMAEOE Modifications and Their Controls

| SEQ ID NO: | Sequence | Backbone | 2'-Modif. | Comments |
|---|---|---|---|---|
| 6 | 5'-TsCsCs GsTsCs AsTsCs Gs CsTs CsCsTs CsAsGs GsG-3' | P = S | 2'-H | parent |
| 7 | 5'-TsCsAs GsTsAs AsTsAs Gs GsCs CsCsAs CsAsTs GsG-3' | P = S | 2'-H | mismatch control |
| 8 | 5'-ToToCo GsTsCs AsTsCs Gs CsTs CoCoTo CoAoGo GoG-3' | P = O/ P = S/ P = O | 2'-O-DMAEOE in the wings | Gapmer (mixed backbone) |
| 9 | 5'-TsCsCs GsTsCs AsTsCs Gs CsTs CsCsTs CsAsGs GsG-3' | P = S | 2'-O-DMAEOE in the wings | Gapmer as uniform thioate |
| 10 | 5'-ToCoAo GsTsAs AsTsAs GsCsCs GsCsCs Gs Co Co CoCoAo CoAoTo GoG-3' | P = O/ P = S/ P = O | 2'-O-DMAEOE in the wings | Gapmer (mixed backbone) |
| 11 | 5'-TsCsAs GsTsAs AsTs As GsCsCs GsCsCs CsCsAs CsAsTs GsC-3' | P = S | 2'-O-DMAEOE in the wings | Gapmer as uniform thioate |
| 12 | 5'-TsCsCs GsTsCs AsTsCs Gs CsTs CsCsTs CsAsGs GsG-3' | P = S | 2'-MOE in the wings | Gapmer with MOE as control |
| 13 | 5'-TsCsAsGsTsAs AsTsAsGsCs CsGsCsCsCsCsAsCsAsTs GsC-3' | P = S | 2'-MOE in the wings | Gapmer with MOE as control | underlined portions of sequences are 2'-deoxy

Proceduer 4
General Procedure for the Evaluation of 2'-O-DMAEOE Oligonucleotides Targeted to HCV Uniformly modified 2'-O-DMAEOE phosphodiester oligonucleotides are evaluated for antisense inhibition of HCV gene via a translation arrest mechanism.

Hepatitis C virus (HCV) is known to be responsible for liver disease in many millions of people throughout the world. HCV is an enveloped, positive-strand RNA virus of the flavivirus family. Initial infections in humans are typically asymptomatic, but chronic infection often ensues in which liver cirrhosis and hepatocellular carcinoma are long-term sequelae. Interferon-α (IFN-α) therapy is widely used in attempts to eradicate the virus from chronically infected individuals, but long-term remissions are achieved in only about 20% of patients, even after 6 months of therapy. So far, there is no antiviral drug available for the treatment of HCV. (Blair et al., 1998). Drug discovery and development efforts have been hampered by the lack of suitable cell culture replication assays for HCV, and vaccine production has been hampered by genetic variability of the virus' envelope genes. Specific inhibitors of cloned viral enzymes such as proteases and the viral polymerase have not yet been reported.

Antisense oligonucleotide therapy represents a novel approach to the control of HCV infection. Several antisense oligonucleotides complementary to HCV RNA sequences adjacent to the polyprotein initiation codon of HCV have been designed at Isis (Hanecak et al., *J. Virol.*, 1996, 70, 5203–5212). The target genome is highly conserved among independent HCV isolates.

It was shown that an RNase H-independent antisense oligonucleotide had greater activity than its parent phosphorothioate (which will work by RNase H mechanism) which was targeted to the AUG site of a core protein sequence of HCV in a human hepatocyte cell line employing a uniformly modified 2'-O-(methoxyethyl) phosphodiester (P=O 20 mer) (Hanecak et al., *J. Virol.*, 1996, 70, 5203–5212). Hepatitis C virus core protein levels were reduced as efficiently as the corresponding 2'-deoxyphosphorothioate with an $IC_{50}$ of 100 nm. SEQ ID NO: 15 was a potent inhibitor of core protein expression without affecting HCV RNA levels. This suggested the inhibition of HCV translation. The parent compound (SEQ ID NO: 14) had Tm of 50.8° C. while the 2'-MOE compound (SEQ ID NO: 15) had a Tm of 83.8° C. Thus, SEQ ID NO: 15 had a better affinity for HCV RNA. The replicative cycle of HCV takes place in the cytoplasm of infected cells, in which RNase H levels have been reported to reduce relative to those of the nucleus. For this reason, it is better to utilize an antisense oligonucleotide which will work by non-RNase H mechanism to inhibit HCV. Oligonucleotide SEQ ID NO: 15 is an attractive lead since it contains a P=O linkage with a 2'-MOE modification. SEQ ID NO: 16 will be tested in accordance with the testing of SEQ ID NO: 14 and 15.

TABLE 4

5'-TTT AGG ATT CGT GCT CAT GG-3'
Antisense Oligonucleotide Targeting HCVC 5'-NCR
Nucleotide Numbers 340–359

| SEQ ID NO: | Backbone | 2'-modification | Tm (° C.) |
|---|---|---|---|
| 14 | P = S | 2'-deoxy | 50.8 |
| 15 | P = O | 2'-MOE | 83.8 |
| 16 | P = O | 2'-2'-O-DMAEOE | |

Procedure 5
In Vitro Assays

Isis antisense oligonucleotides complementary to the HCV polyprotein initiation codon sequence are known to inhibit expression of the viral core protein in immortalized cell lines engineered to express HCV RNA from recombinant DNA integrated into the host cell genome (Hanecak ibid). Non-complementary control oligonucleotides have no effect on HCV RNA or protein levels in this system. H8Ad17C cells will be treated with a range of concentration of oligonucleotides shown in Table 4 above, especially SEQ ID NO: 16, (0–200 nm) in the presence of cationic lipids and total protein levels will be evaluated 20 hours later by western blot analysis.

Procedure 6
In Vivo Model for HCV

Animal models of HCV infection are not readily available. An alternative approach has been developed to evaluate antisense oligonucleotides to inhibit HCV gene expression in livers of mice. For these experiments, HCV sequences, including SEQ ID NO: 15 target sequence, were fused to a luciferase reporter gene and inserted into a Vaccinia virus. Infection of mice with this recombinant vaccination virus results in quantifiable levels of luciferase in liver tissue. Potent phosphorothioate antisense oligonucleotides have been shown to work in this model. SEQ ID NO: 16 (the 2'-O-DMAEOE RNA analog of SEQ ID NO: 15) will be evaluated for inhibition of expression of the HCV-luciferase construct in livers of mice infected with the recombinant vaccinia virus. Inhibition will be evaluated for sequence-dependency and dose response. HCV-luciferase expression in livers of mice infected with a control vaccinia virus vector lacking HCV target sequences will be used as control and the effect of antisense drug in these control systems will be evaluated. (Antisense oligonucleotide-mediated inhibition of hepatitis C virus gene expression in mouse liver (Anderson et al., Meeting Abstracts, International Hepatitis Meeting, Hawaii, 1997).

Procedure 7
In Vivo Nuclease Resistance

The in vivo Nuclease Resistance of gapmers having the 2'-O-DMAEOE is studied in mouse plasma and tissues (kidney and liver). For this purpose, the C-raf oligonucleotide series SEQ ID NO: 17 will be used and the following five oligonucleotides listed in Table 5 below will be evaluated for their relative nuclease resistance.

TABLE 5

| SEQ ID NO: | Sequence | Backbone | Description |
|---|---|---|---|
| 17 | 5'-ATG CAT TCT GCC CCA AGGA-3' | P = S, 2'-H | (control) rodent C-raf antisense oligo |
| 18 | AoToGoCoAsTsTsCsTsGs CsCsCsCsAoAoGoGoA | P = O/P = S/ P = O | (control) 2'-MOE/2'-H/ 2'-MOE |
| 19 | AsTsGsCsAsTsTsCsTsGs CsCsCsCsAsAsGsGsA | P = S | (control) 2'-MOE/2'-H/2'-MOE |
| 20 | AoToGoCoAsTsTsCsTsGs CsCsCsCsAoAoGoGoA | P = O/P = S/ P = O | 2'-2'-O-DMAEOE/ 2'-H/2'-2'-O-DMAEOE |
| 21 | AsTsGsCsAsTsTsCsTsGs CsCsCsCsAsAsGsGsA | P = S | 2'-2'-O-DMAEOE/ 2'-H/2'-2'-O-DMAEOE |

Procedure 8
Animal Studies

For each oligonucleotide to be studied, 9 male BALB/c mice (Charles River, Wilmington, Mass.), weighing about 25 g are used (Crooke et al., *J. Pharmacol. Exp. Ther.*, 1996, 277, 923). Following a 1-week acclimation, the mice receive a single tail vein injection of oligonucleotide (5 mg/kg) administered in phosphate buffered saline (PBS), pH 7.0. The final concentration of oligonucleotide in the dosing solution is (5 mg/kg) for the PBS formulations. One retro-orbital bleed (either 0.25, 9.05, 2 or 4 post dose) and a terminal bleed (either 1, 3, 8 or 24 h post dose) is collected from each group. The terminal bleed (approximately 0.6–0.8 mL) is collected by cardiac puncture following ketamine/ xylazine anesthesia. The blood is transferred to an EDTA-coated collection tube and centrifuged to obtain plasma. At termination, the liver and kidneys will be collected from each mouse. Plasma and tissues homogenates will be used for analysis for determination of intact oligonucleotide content by CGE. All samples will be immediately frozen on dry ice after collection and stored at −80° C. until analysis.

Procedure 9

The binding affinity as measured by Tm was evaluated for oligonucleotides having the 2'-O-[2-(2-N,N-dimethylaminoethyl)oxyethyl] modification. 5-methyl-2'-O-[2-(2-N,N-dimethylaminoethyl)oxyethyl] (modified T) was incorporated at selected positions in oligonucloetides and binding was measured to complementary RNA oligonucleotides.

TABLE 6

| SEQ ID NO: | Sequence | Backbone | Mass Calculated | Mass Observed |
|---|---|---|---|---|
| 22 | TCC AGG TGT CCG CAT C | PO | 5660.3[a] | 5659.1[a] |
| 23 | CTC GTA CTT TTC CGG TCC | PO | 5912.2 | 5913.5 |
| 24 | GCG TTT TTT TTT TGC G | PO | 6487.3[a] | 6488.5[a] |
| 25 | GAT CT | PO | 1910.6[a] | 1910.8[a] |
| 26 | TTT TTT TTT TTT TTT TTT T | PO | 6544.7[a] | 6542.62[a] |

[a] as DMT-on, underlined nucleosides are 2'-O-[2-(2-N,N-dimethylaminoethyl)oxyethyl]-5-methyl uridine (2'-sub-T)

TABLE 7

| SEQ ID NO: | Sequence | Target DNA Tm | ΔTm | ΔTm/ mod. | Target RNA Tm | ΔTm | ΔTm/ mod. |
|---|---|---|---|---|---|---|---|
| 27 | TCC AGG TGT CCG CAT C | not determined | | | 62.3 | | |
| 22 | TCC AGG TGT CCG CAT C | not determined | | | 65.6 | 3.3 | 0.83° |
| 28 | GCG TTT TTT TTT TGC G | 54.2 | | | 48.1 | | |
| 24 | GCG TTT TTT TTT TGC G | 50.0 | −4.1 | −4.1 | 59.7 | 10.6 | 1.1° |

Underlined nucleosides are 2'-O-[2-(2-N,N-dimethylaminoethyl)oxyethyl] modified.

The 2'-O-[2-(2-N,N-dimethylaminoethyl)oxyethyl] modified nucleotides show increased Tm as compared to unmodified DNA as shown in Table 7.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An oligonucleotide having at least one nucleoside of formula:

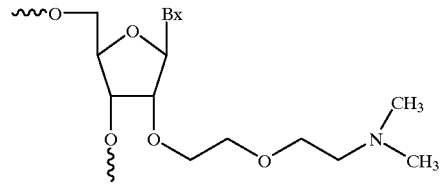

wherein Bx is a heterocyclic base.

2. The oligonucleotide of claim 1 wherein said heterocyclic base is a purine or a pyrimidine.

3. The oligonucleotide of claim 2 wherein said purine or said pyrimidine is adenine, cytosine, 5-methylcytosine, thymine, uracil, guanine or 2-aminoadenine.

4. The oligonucleotide of claim 1 comprising from about 5 to about 50 nucleosides.

5. The oligonucleotide of claim 1 comprising from about 8 to about 30 nucleosides.

6. The oligonucleotide of claim 1 comprising from about 15 to about 25 nucleosides.

7. A compound having the formula:

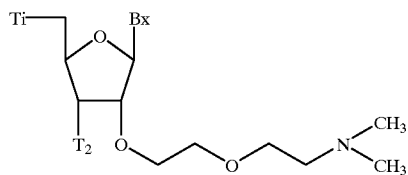

wherein:

Bx is a heterocyclic base; and $T_1$ and $T_2$, independently, are OH, a protected hydroxyl, an activated phosphate group, an activated phosphite group, a reactive group for forming an internucleotide linkage, a nucleotide, a nucleoside, or an oligonucleotide.

8. The oligonucleotide of claim 7 wherein said heterocyclic base is a purine or a pyrimidine.

9. The oligonucleotide of claim 8 wherein said purine or said pyrimidine is adenine, cytosine, 5-methylcytosine, thymine, uracil, guanine or 2-aminoadenine.

* * * * *

(12) REEXAMINATION CERTIFICATE (4819th)
United States Patent
Manoharan et al.

(10) Number: US 6,043,352 C1
(45) Certificate Issued: Jul. 22, 2003

(54) 2'-O-DIMETHYLAMINOETHYLOXYETHYL-MODIFIED OLIGONUCLEOTIDES

(75) Inventors: Muthiah Manoharan, Carlsbad, CA (US); Phillip Dan Cook, Lake San Marcos, CA (US)

(73) Assignee: Isis Pharmaceuticals, Inc., Carlsbad, CA (US)

Reexamination Request:
No. 90/006,207, Jan. 28, 2002

Reexamination Certificate for:
Patent No.: 6,043,352
Issued: Mar. 28, 2000
Appl. No.: 09/130,566
Filed: Aug. 7, 1998

(51) Int. Cl.[7] ............ C12Q 1/68; C07H 21/00; C07H 21/02; C07H 21/04

(52) U.S. Cl. .......... 536/24.2; 435/6; 536/24.5; 536/26.6

(58) Field of Search ............ 435/6; 536/24.2, 536/24.5, 26.6

(56) References Cited

FOREIGN PATENT DOCUMENTS

WO    WO 97/46569    12/1997

*Primary Examiner*—Jezia Riley

(57) ABSTRACT

2'-O-Modified ribosyl nucleosides and modified oligonucleotides containing such nucleotides are disclosed. Oligonucleotides are disclosed that have increased binding affinity as shown by molecular modeling experiments. The 2'-O-modified nucleosides of the invention include ring structures that position the sugar moiety of the nucleosides preferentially in 3' endo geometries.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *